US00PP20498P2

(12) United States Plant Patent
Kempen

(10) Patent No.: US PP20,498 P2
(45) Date of Patent: Nov. 17, 2009

(54) ***ECHINACEA* PLANT NAMED 'MISTRAL'**

(50) Latin Name: *Echinacea purpurea*
Varietal Denomination: Mistral

(75) Inventor: Antonius Johannes Maria Kempen, Mijdrecht (NL)

(73) Assignee: Inspiration Plant, Heerhugowaard (NL)

( * ) Notice: Subject to any disclaimer, the term of this patent is extended or adjusted under 35 U.S.C. 154(b) by 0 days.

(21) Appl. No.: 12/150,431

(22) Filed: Apr. 28, 2008

(51) Int. Cl.
*A01H 5/00* (2006.01)

(52) U.S. Cl. ..... Plt./428

(58) Field of Classification Search ..... Plt./428
See application file for complete search history.

*Primary Examiner*—Annette H. Para
*Assistant Examiner*—Susan B McCormick Ewoldt
(74) *Attorney, Agent, or Firm*—Jondle & Associates, P.C.

(57) ABSTRACT

An *Echinacea* cultivar particularly distinguished by its extremely compact growth, red-purple flowers, very rich flowering due to branched peduncles and strong peduncles, is disclosed.

2 Drawing Sheets

Genus and species: *Echinacea purpurea.*
Variety denomination: 'Mistral'.

BACKGROUND OF THE NEW PLANT

The present invention comprises a new and distinct cultivar of *Echinacea*, botanically known as *Echinacea purpurea*, and hereinafter referred to by the cultivar name 'Mistral'. The new cultivar originated from a naturally-occurring branch mutation of the *Echinacea purpurea* cultivar 'Kim's Knee High', U.S. Plant Pat. No. 12,242 discovered in 2005 in an outdoor nursery of the inventor in Mijdrecht, The Netherlands.

The new cultivar was discovered in 2005 in Mijdrecht, The Netherlands, and has been asexually reproduced repeatedly by tissue culture in Schagen, The Netherlands over a three-year period. The present invention has been found to retain its distinctive characteristics through successive asexual propagations.

Plant Breeder's Rights for this cultivar have been applied for in the European Union on Oct. 11, 2007. 'Mistral' has not been made publicly available more than one year prior to filing of this application.

SUMMARY OF THE INVENTION

The following are the most outstanding and distinguishing characteristics of the new cultivar when grown under normal horticultural practices in Schagen, The Netherlands.

1. Extremely compact growth;
2. Red-purple flowers;
3. Very rich flowering due to branched peduncles; and
4. Strong peduncles.

DESCRIPTION OF THE PHOTOGRAPHS

This new *Echinacea* plant is illustrated by the accompanying photographs which show overall plant habit including inflorescences, buds, and foliage of the plant; the colors shown are as true as can be reasonably obtained by conventional photographic procedures. The photos are of a 2-year-old plant grown in a 19-cm pot outdoors in late summer 2007 in Mijdrecht, The Netherlands.

DESCRIPTION OF THE NEW CULTIVAR

Figure 1:
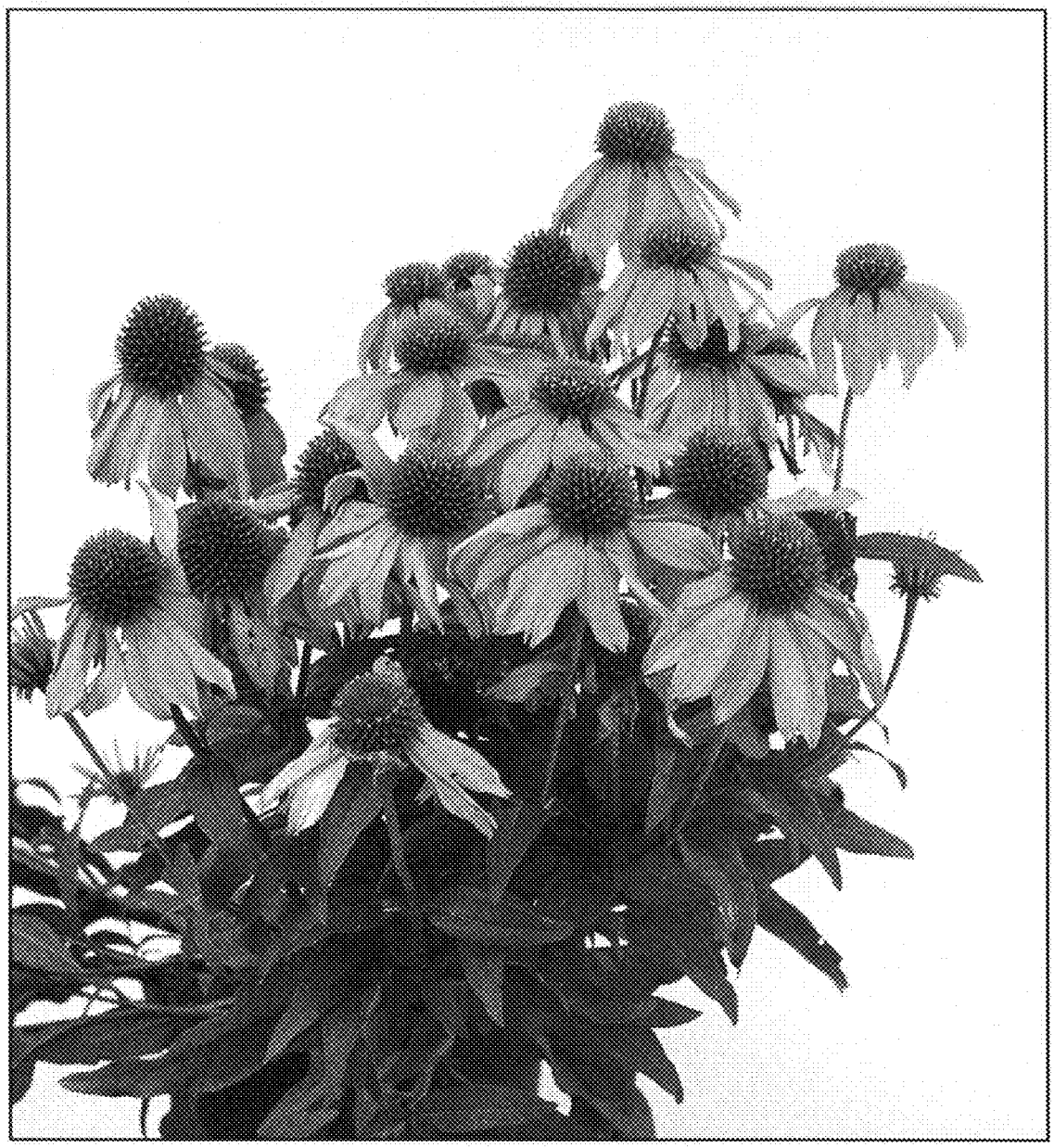
FIG. 1 shows the overall plant habit including inflorescences and foliage.
Figure 2:
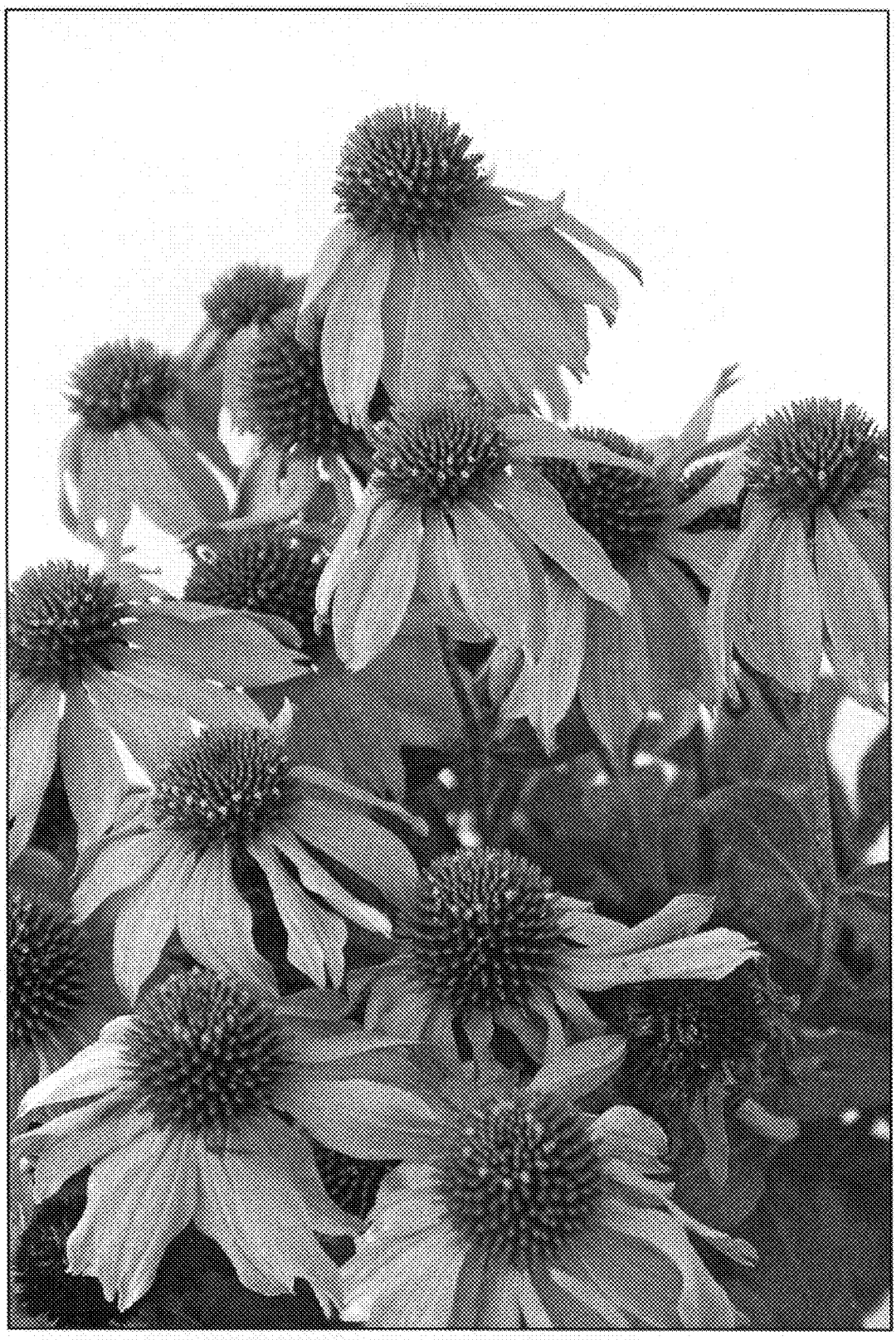
FIG. 2 shows a closer view of the inflorescences.

The following detailed descriptions set forth the distinctive characteristics of 'Mistral'. The data which define these characteristics were collected from asexual reproductions carried out in Schagen, The Netherlands. The plant history was taken on 2-year-old, un-pinched plants grown in 19-cm pots outdoors during late summer. The range of daytime temperature was 12° C. to 30° C. and the range of night-time temperature was from 5° C. to 15° C. No growth retardants were used. The color readings were determined under natural light. Color references are to The R.H.S. Colour Chart of The Royal Horticultural Society of London (R.H.S.) (2001).

DESCRIPTION OF THE NEW PLANT

Classification:
- *Family.*—Asteraceae.
- *Botanical name.*—*Echinacea purpurea.*
- *Common name.*—Coneflower, *echinacea.*

Parentage: Naturally-occurring branch mutation of *Echinacea purpurea* 'Kim's Knee High' (U.S. Plant Pat. No. 12,242).

Plant:
- *Form and habit.*—Herbaceous perennial.
- *Growth and branching habit.*—Broadly upright with flowering stems growing from the base; grows about 10 cm per month in the spring.
- *Plant shape.*—Broadly ovate.
- *Height (from top of soil, including inflorescences).*—36.8 cm.
- *Width.*—50.0 cm.
- *Vigor.*—Moderate to moderately low.
- *Time to produce a finished flowering plant.*—About 20 weeks.

*Outdoor plant performance.*—Use as bedding plants or in mixed-container plantings; tolerant to temperatures up to 35° C.; hardy to USDA zones 3 or 4.

*Time to initiate and develop roots.*—About 6 weeks in winter.

*Root description.*—Fibrous, medium thickness, light brown and freely branching; dense roots.

Stems:

*Branching.*—Basal; no pinching required.

*Total number of branches.*—7.

*Length.*—24.1 cm.

*Diameter.*—0.7 cm.

*Internode length.*—3.5 cm.

*Appearance.*—Rounded.

*Strength.*—Strong.

*Aspect.*—90° (straight up) to 40°.

*Color.*—RHS 144B (Yellow-green); RHS 144A towards the base.

*Texture.*—Stems densely covered with short strigose hairs Length of hairs: 0.1 cm Color of hairs: RHS 157A to RHS 157D (Green-white).

Leaves:

*Arrangement.*—Simple and alternate.

*Shape.*—Narrow ovate to lanceolate, moderately carinate.

*Apex.*—Acute.

*Base.*—Attenuate.

*Margin.*—Entire, undulate.

*Size.*—Length: 11.5 cm Width: 4.0 cm.

*Immature leaf.*—Color: Upper surface: RHS 137B (Green) Lower surface: RHS 137C (Green).

*Mature leaf.*—Color: Upper surface: RHS 137A to RHS 137B (Green) Lower surface: RHS 147B (Yellow-green).

*Texture* (*both surfaces*).—Slightly glossy, rough to the touch.

*Pubescence.*—Both sides of leaf and margins moderately densely covered with short strigose hairs. Length of hairs: 0.03 cm Color of hairs: Ranging from RHS 157A to RHS 157D (Green-white).

*Venation.*—Pinnate.

*Vein color.*—Upper surface: RHS 150D (Yellow-green) Lower surface: RHS 145C (Yellow-green).

Petioles:

*Length.*—3.8 cm; petioles shorter towards the tops of the stem.

*Diameter.*—Petiole is v-shaped; average width is 0.6 cm and average height is 0.4 cm.

*Color.*—Upper surface: RHS 145B (Yellow-green) with RHS 141A (Green) margins Lower surface: RHS 145A (Yellow-green) with RHS 144A (Green) margins.

*Texture* (*both surfaces*).—Slightly glossy, smooth, but margins sparsely covered with very short strigose hairs Length of hairs: 0.03 cm Color of hairs: Ranging from RHS 157A to RHS 157D (Green-white).

Inflorescence buds:

*Shape.*—Flattened globular with immature ray florets pointing upwards.

*Length.*—2.6 cm.

*Diameter.*—1.9 cm.

*Color.*—RHS 143A to RHS 143B (Green); immature ray florets RHS N144A to RHS 145A (Yellow-green).

Inflorescence:

*Type.*—Capitulum.

*Arrangement.*—Terminal capitulae.

*Shape.*—Terminal capitulum consisting of numerous disc florets, one row of ray florets and three rows of involucral bracts.

*Blooming habit.*—Continuously flowers from early July to mid-September.

*Quantity of open inflorescences per stem.*—11.

*Quantity of buds per stem.*—5.

*Quantity of open inflorescences and buds per plant.*—110.

*Rate of inflorescence opening.*—The terminal inflorescence of a stem opens first, followed by the secondary, tertiary, etc.

*Lastingness of the inflorescences on the plant.*—About 2 weeks.

*Fragrance.*—Faint sweet fragrance.

*Inflorescence size.*—Height: 4.3 cm (excluding peduncle) Diameter: 6.5 cm.

*Disc diameter.*—1.2 cm.

*Persistent or self-cleaning.*—Self-cleaning.

Disc floret:

*Arrangement.*—Spirally placed on the disc.

*Quantity per inflorescence.*—320.

*Shape.*—Tubular.

*Apex.*—Acute, upper 15% free.

*Base.*—Fused.

*Margin.*—Entire, upper 15%; lower 85% fused into a tube.

*Size.*—Length: 0.75 cm Diameter: 0.2 cm.

*Texture* (*both surfaces*).—Smooth, slightly glossy.

*Color, when opening* (*both surfaces*).—RHS 144C to RHS 144D (Yellow-green); RHS 144B to RHS 144C (slightly darker Yellow-green) towards the tip.

*Color, when fully opened* (*both surfaces*).—Between RHS N144A to RHS 151A (Yellow-green).

Ray floret:

*Arrangement.*—Rotate.

*Quantity per inflorescence.*—13.

*Number of whorls.*—1.

*Shape.*—Oblanceolate.

*Aspect.*—Downward, average angle 145°.

*Apex.*—Emarginate to praemorse.

*Base.*—Cuneate.

*Margin.*—Entire.

*Texture.*—General: Smooth, very slightly glossy Upper surface: Smooth, slightly ribbed lengthwise Lower surface: Smooth, ribbed lengthwise.

*Size.*—Length: 3.5 cm Width: 1.2 cm.

*Color, when opening.*—Upper surface: RHS 61C (Red-purple) with colors between RHS 63C to RHS 64D (lighter Red-purple) towards the tip Lower surface: RHS 63C (Red-purple) with RHS 144A to RHS 144B (Yellow-green) at the tip.

*Color, when fully opened.*—Upper surface: Between RHS 61D to RHS 64D (Red-purple) with RHS 63C and RHS 63D to RHS 65A (lighter Red-purple) towards the tip Lower surface: RHS 64D (Red-purple) with RHS 144A to RHS 144B (Yellow-green) at the tip.

*Color, fading to.*—Upper surface: RHS 70C to RHS 70D (Red-purple) Lower surface: RHS 70C (Red-purple) with RHS 143C to RHS 144A (Yellow-green) tip and central band.

Peduncle:

*Length, terminal peduncle.*—21.3 cm.

*Length, fourth peduncle.*—17.8 cm.

*Length, seventh peduncle.*—17.2 cm.

*Diameter.*—0.3 cm.

*Aspect/angle.*—Straight on top of flowering stem.

*Strength.*—Strong.

*Texture.*—Slightly rough to the touch; moderately covered with short strigose hairs Length of hairs: 0.05 cm Color of hairs: Ranging from RHS 157A to RHS 157D (Green-white).

*Color.*—RHS 144A to RHS 144B (Yellow-green).

Bracts:

*Arrangement.*—Rotate, placed in three rows.

*Number of bracts per inflorescence.*—40.

*Appearance.*—Dull, tough.

*Shape.*—Lanceolate, curved towards the peduncle.

*Apex.*—Acute.

*Base.*—Cuneate.

*Margin.*—Entire.

*Texture.*—Upper surface: Smooth Lower surface and margins: Densely covered with short hairs Length of hairs: 0.05 cm Color of hairs: Ranging from RHS 157A to RHS 157D (Green-white).

*Size.*—Length: 0.7 cm Width: 0.15 cm.

*Color.*—Upper surface: RHS 141A (Green) Lower surface: RHS 137A with RHS 143D (Light-green) at the base.

Receptacles:

*Shape.*—Triangular.

*Size.*—Height: 0.8 cm Diameter: 0.6 cm Color: RHS 155A (White).

*Receptacle spines.*—Number of spines per disc: 320 Shape: Acicular Apex: Acute Base: Attenuate Texture: Smooth, glossy Color: Apex: RHS N30A (Red) Mid-section: RHS 24A (Orange) Base: RHS 144B (Yellow-green).

Reproductive organs:

*Androecium.*—Location: Present on disc florets only Stamens: Number: 5, per floret Filament length: 0.25 cm Filament color: RHS 145C (Yellow-green) Anther shape: Basifixed Anther length: 0.3 cm Anther color: RHS N200A (Brown) Pollen color: RHS 17A (Yellow-orange) Pollen amount: Moderate to high.

*Gynoecium.*—Location: Present on ray and disc florets Number: One per floret Pistil length: 0.6 cm Stigma color: RHS 53A (Red) Stigma shape: Decurrent Style color: RHS 42D (Red) Style length: 0.4 cm

*Ovary color.*—RHS 145D (Yellow-green).

Fruit and seed set: No seed set observed.

Disease and insect resistance: Average/typical of the species; no special observations made.

COMPARISON WITH PARENTAL AND COMMERCIAL CULTIVARS

'Mistral' differs from the parent 'Kim's Knee High' (U.S. Plant Pat. No. 12,242) in that 'Mistral' has more flowers per plant than 'Kim's Knee High'. In addition, 'Mistral' has yellow-green disc florets while 'Kim's Knee High' has purple to greyed-purple disc florets.

'Mistral' differs from the cultivar 'Fatal Attraction' (U.S. Plant Pat. No. 18,429) in that 'Mistral' has a smaller plant habit and shorter stems. In addition, 'Mistral' has different colored ray and disc florets than 'Fatal Attraction'.

I claim:

1. A new and distinct cultivar of *Echinacea* plant, as shown and described herein.

* * * * *